United States Patent
Nakahara et al.

(10) Patent No.: US 7,135,043 B2
(45) Date of Patent: Nov. 14, 2006

(54) INTERVERTEBRAL CAGE

(75) Inventors: Shinnosuke Nakahara, Okayama (JP); Kazuhiro Hasegawa, Niigata (JP); Kazuya Oribe, Tokyo (JP); Hiroshi Takamido, Aichi (JP)

(73) Assignee: Showa Ika Kohgyo Co., Ltd., Aichi (JP)

( * ) Notice: Subject to any disclaimer, the term of this patent is extended or adjusted under 35 U.S.C. 154(b) by 0 days.

(21) Appl. No.: 10/642,684

(22) Filed: Aug. 19, 2003

(65) Prior Publication Data

US 2004/0172130 A1 Sep. 2, 2004

(30) Foreign Application Priority Data

Aug. 20, 2002 (JP) .............................. 2002-239095

(51) Int. Cl.
*A61F 2/44* (2006.01)
(52) U.S. Cl. ................................. 623/17.11
(58) Field of Classification Search ... 623/17.11–17.16
See application file for complete search history.

(56) References Cited

U.S. PATENT DOCUMENTS

| | | | |
|---|---|---|---|
| 5,397,364 A | 3/1995 | Kozak et al. | |
| 6,432,106 B1 * | 8/2002 | Fraser | 606/61 |
| 6,527,803 B1 | 3/2003 | Crozet et al. | |
| 6,716,245 B1 | 4/2004 | Pasquet et al. | |
| 2002/0022886 A1 * | 2/2002 | Fuss et al. | 623/17.11 |
| 2002/0052656 A1 | 5/2002 | Michelson | |
| 2003/0130737 A1 * | 7/2003 | McGahan et al. | 623/17.11 |
| 2003/0181981 A1 * | 9/2003 | Lemaire | 623/17.11 |
| 2004/0172133 A1 * | 9/2004 | Gerber et al. | 623/17.11 |

FOREIGN PATENT DOCUMENTS

| | | |
|---|---|---|
| FR | 2779941 | 12/1999 |
| JP | 9-503416 | 4/1997 |
| JP | 2002-095685 | 4/2002 |
| WO | 02/03895 | 1/2002 |
| WO | 02/36049 | 5/2002 |

OTHER PUBLICATIONS

English Language Abstract of JP-2002-095685.

* cited by examiner

*Primary Examiner*—Bruce Snow
(74) *Attorney, Agent, or Firm*—Greenblum & Bernstein, P.L.C.

(57) ABSTRACT

An intervertebral cage of the present invention includes main body defined by an upper surface, a lower surface, and a pair of side surfaces. A withdrawal prevention portion is provided on the upper and/or the lower surfaces of the main body and asymmetrically with respect to the side surfaces in a top or bottom plan view. The withdrawal prevention portion regulates an insertion direction of the intervertebral cage.

4 Claims, 6 Drawing Sheets

INTERVERTEBRAL CAGE

CROSS REFERENCE TO RELATED APPLICATIONS

This application is based upon and claims the benefit of priority from the prior Japanese Patent Applications No. P2002-239095 filed on Aug. 20, 2002; the entire contents of which are incorporated herein by reference.

BACKGROUND OF THE INVENTION

1. Field of the Invention

The invention relates to an intervertebral cage that can be inserted between upper and lower vertebrae in longitudinal and slating directions after an intervertebral disk is removed.

2. Description of the Related Art

There have been known intervertebral cages inserted between the vertebrae the intervertebral disk of which is removed.

FIGS. 1 and 2 show an intervertebral cage of a related art of this invention (Japanese Unexamined Patent Publication No. 9-503416). In the related art, an intervertebral cage 50 is comprised of a pair of left and right semicircular lateral spacers 51A, 51B; front and rear central spacers 53A, 53B are integrally fixed to each other by left and right fixing screws 55. This intervertebral cage 50 is inserted between upper and lower vertebrae 59U, 59L after an intervertebral disk is removed. The central spacers 53A, 53B and lateral spacers 51A, 51B define a cavity 70.

The related art has a problem that 1) since the intervertebral cage 50 is comprised of a large number of components and has a complex structure, and 2) does not have protrusions for preventing itself from coming off, it can not sufficiently be fixed between the vertebrae after it is inserted between the vertebrae.

Further, in the related art, it is premised that the intervertebral cage 50 is inserted between the upper and lower vertebrae from an anterior side but is not inserted from longitudinal and slanting anterior sides. Thus, an improved intervertebral cage has been desired.

SUMMARY OF THE INVENTION

This invention has been made to solve the above-mentioned problems. According to an aspect of the invention, there is provided an intervertebral cage inserted between vertebrae of a spine comprising: a main body defined by a pair of upper and lower surfaces and a pair of side surfaces connected thereto; and withdrawal prevention means formed on the upper and/or lower surfaces of the main body and asymmetrically in a sectional side view, wherein the withdrawal prevention means (e.g. withdrawal prevention portions) regulates an insertion direction of the intervertebral cage.

DETAILED DESCRIPTION OF THE INVENTION

An embodiment according to the present invention will be described with reference to FIGS. 3 to 8B.

An intervertebral cage 41 includes a hollow main body 43 and withdrawal prevention means integrally formed on the upper and lower surfaces of the main body 43.

Figure 1:
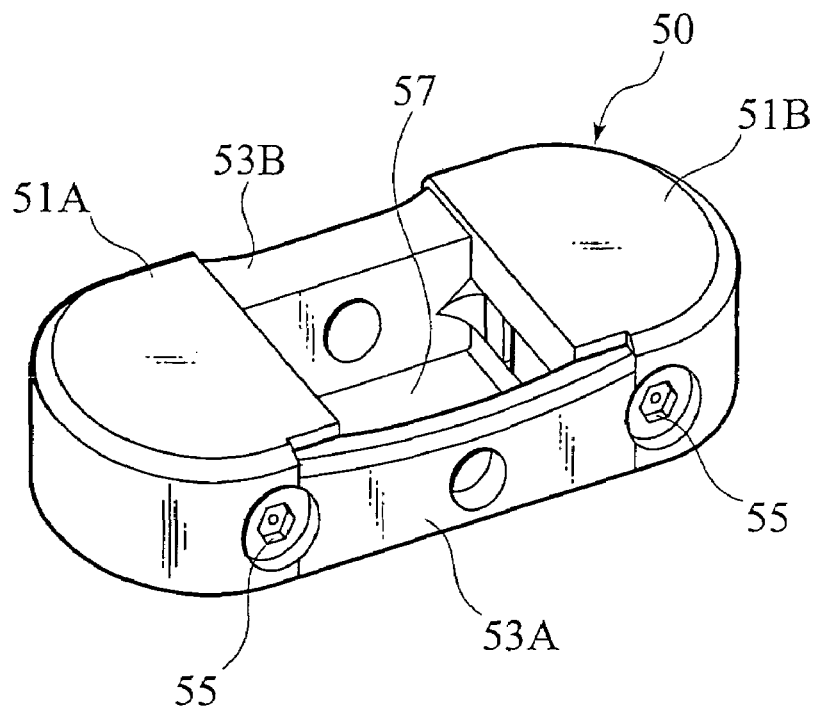
FIG. 1 is a perspective view of a conventional intervertebral cage.
Figure 2:
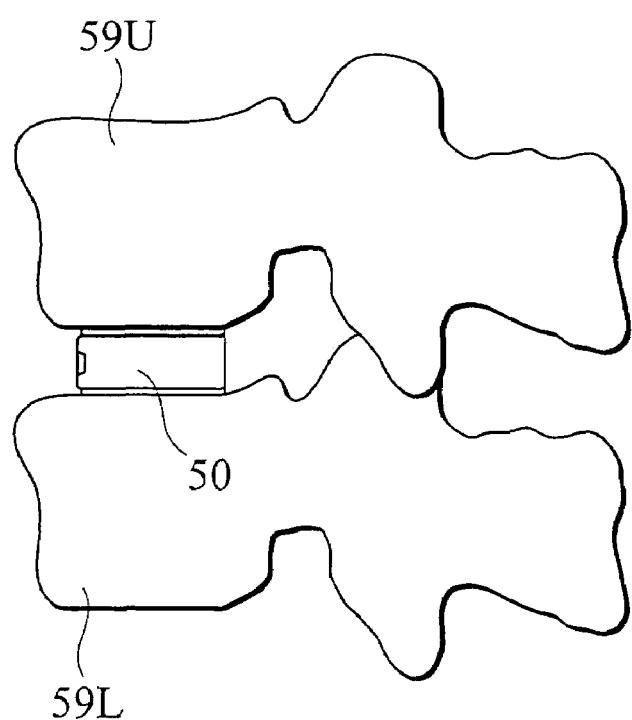
FIG. 2 is a side view of a conventional intervertebral cage inserted between the intervertbrae.
Figure 3:
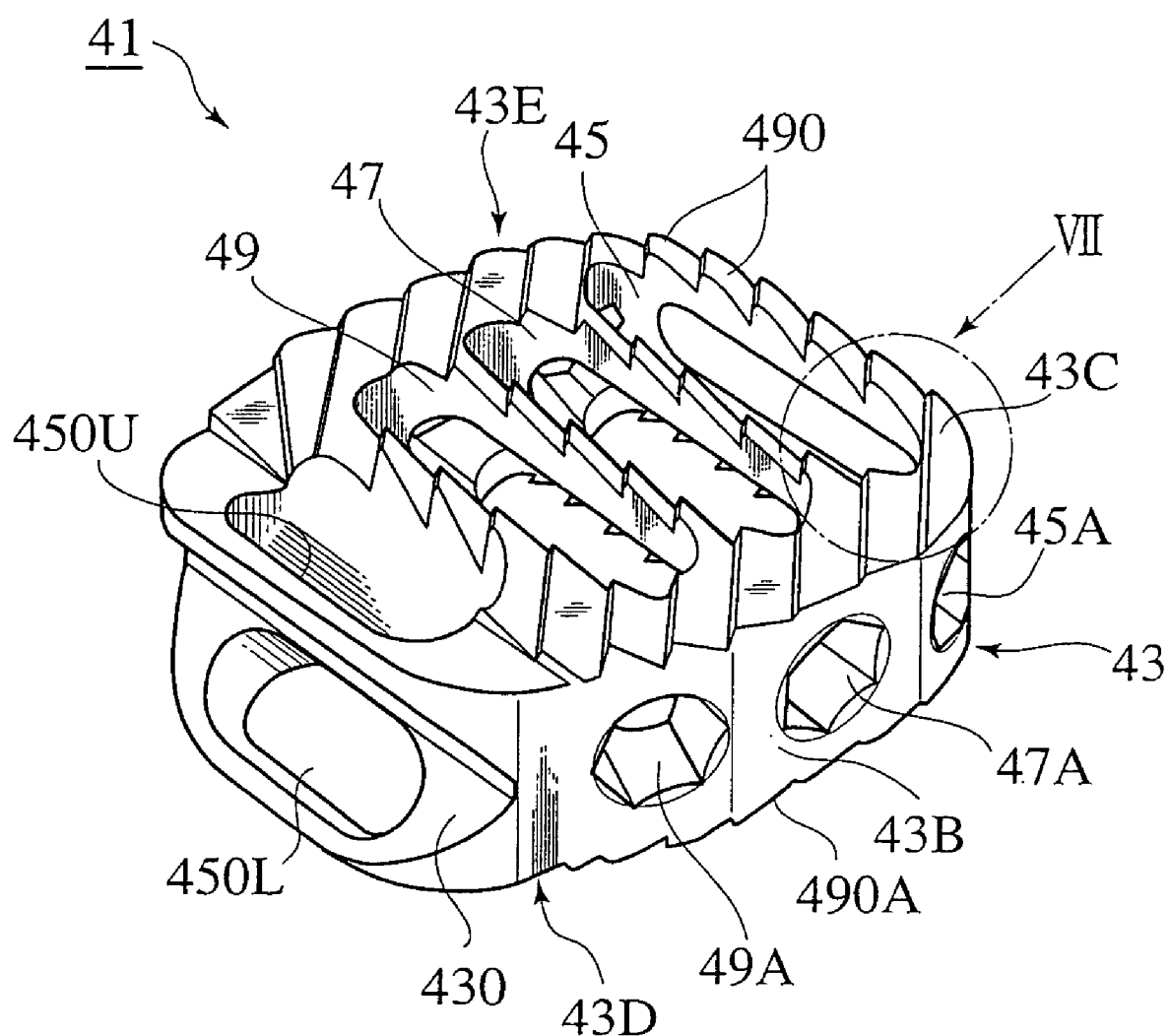
FIG. 3 is a perspective view of an intervertebral cage of the present invention.
Figure 4A:
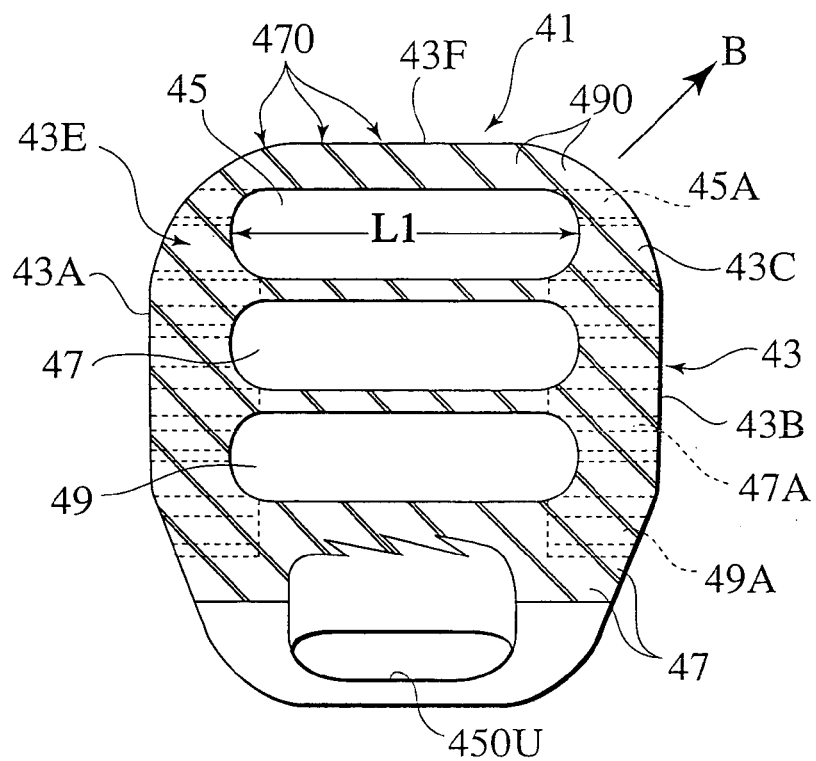
FIG. 4A is a plan (top plan) view of the intervertebral cage of the present invention.
Figure 4B:
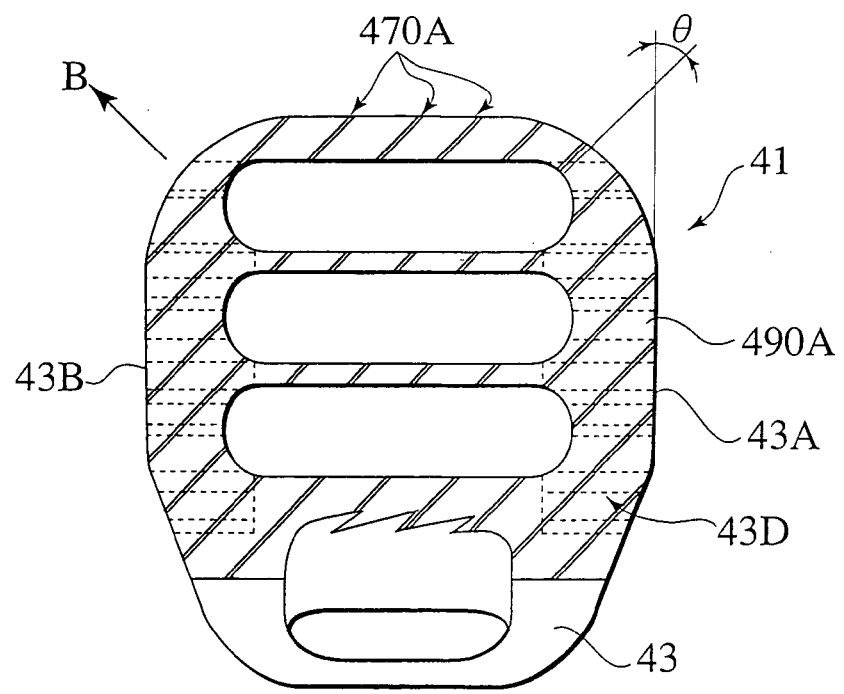
FIG. 4B is a plan (bottom) view of the intervertebral cage of the present invention.
Figure 5:
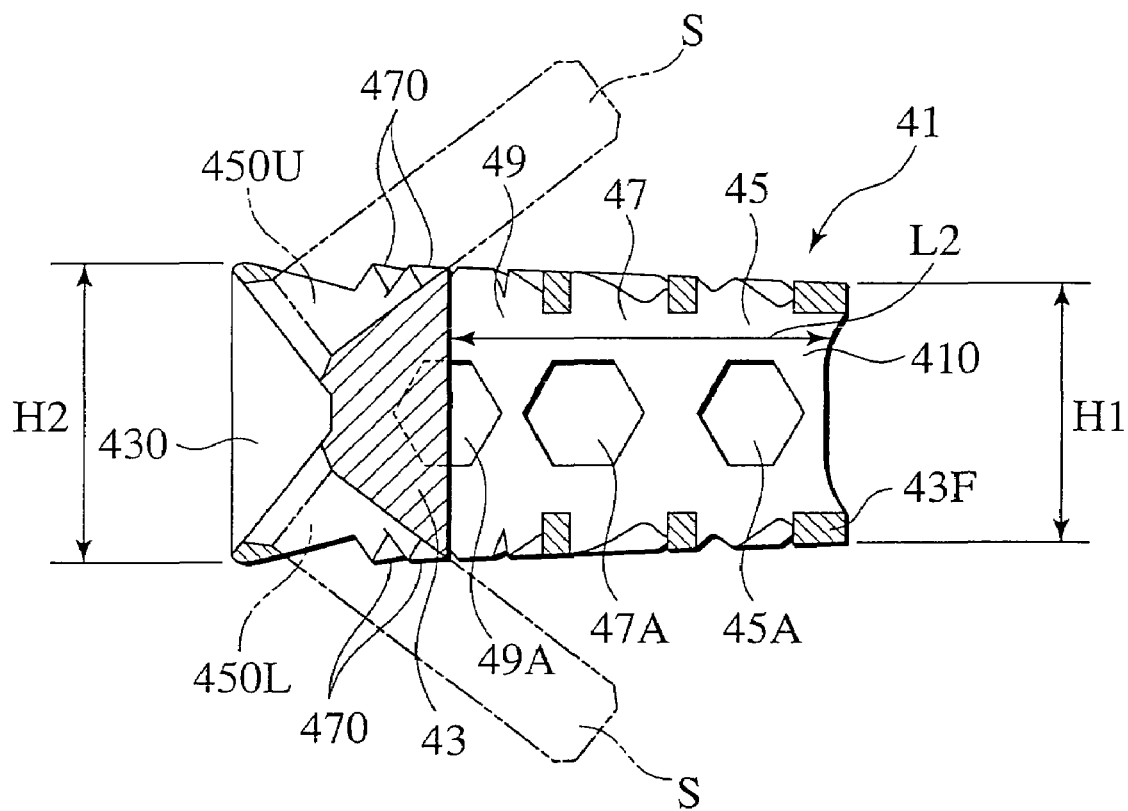
FIG. 5 is a sectional side view of the intervertebral cage of the present invention.
Figure 6:
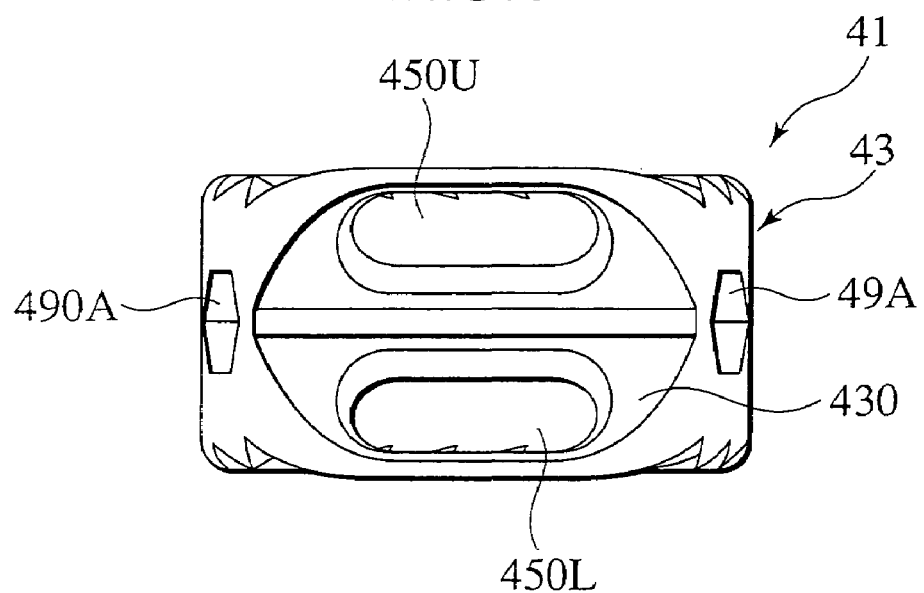
FIG. 6 is a rear view of the intervertebral cage of the present invention.

As shown in FIGS. 4A and 4B, the main body 43 is roughly formed in a deformed hexagon, and each corner is formed in a circular arc. Further, as shown in FIG. 5, the thickness H2 of the rear end side of the main body 43 is larger than the thickness H1 of the front end side (tip end side) of the main body 43.

A front hole 45, a center hole 47 and a rear hole 49 each having a length L1 are respectively formed in the front side (43F side), the central portion and the rear side portion of the main body 43 from an upper surface 43E of the main body 43 to a lower surface 43D in the longitudinal direction with respect to the direction in which the intervertebral cage 41 is inserted. Further, a hole 410 (see FIG. 5) that is formed in the cross direction and made nearly equal in length in the longitudinal direction to the respective holes 45, 47 and 49 (that is, the length L1 shown in FIG. 4A is nearly equal to the length L2 shown in FIG. 5) is formed in the main body 43 from a front surface 43F to the rear hole 49.

Since the front hole 45, the center hole 47, the rear hole 49 and the hole 410 are formed in the main body 43, the main body 43 is formed in a hollow body. Transverse through holes 45A, 47A and 49A are respectively formed at positions corresponding to the front hole 45, the center hole 47 and the rear hole 49 in the both side surfaces 43A and 43B of the main body 43 (see FIG. 3).

Further, a groove 430 formed in the V-shaped in a sectional side view is made in the rear end surface of the main body 43. Upper and lower screw through holes 450U and 450L made through the upper surface 43E and lower surface 43D are formed in the groove 430 in the slanting and vertical direction. Each of these screw through holes 450U and 450L is formed in a hole elongated in the longitudinal direction.

Figure 7:
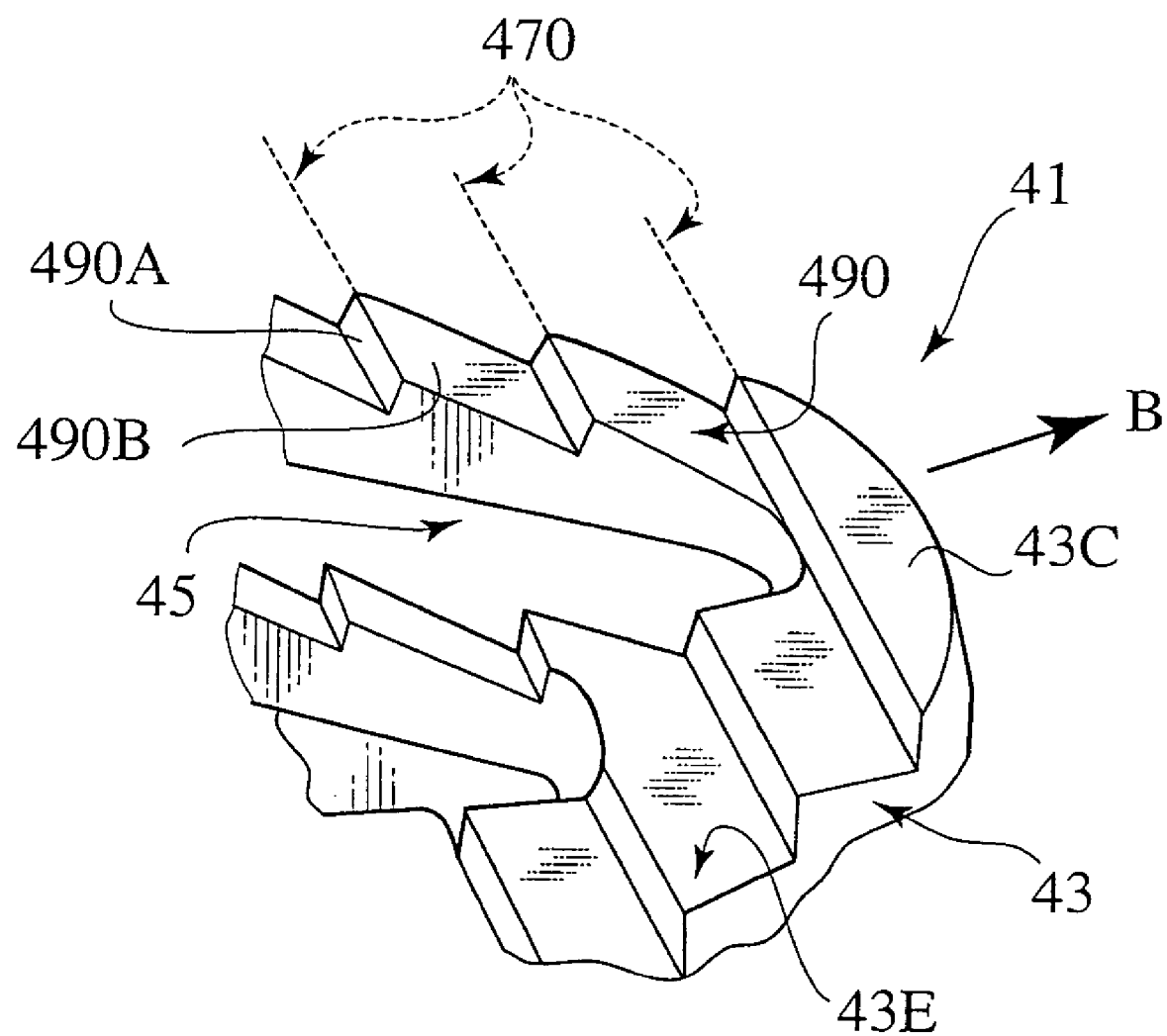
FIG. 7 is a partially enlarged view of FIG. 3.

The withdrawal prevention means according to the present invention will be described with reference to FIG. 7.

In a corner 43C, a plurality of notches (claw portions 490) are formed in parallel to a line 470 perpendicular to a bisector of a vertical angle formed by the side surface 43B and the front surface 43F. Each of the plurality of claw portions 490 is nearly formed in a wedge shape, and one surface 490A of the claw portions 490 is set at a length shorter than that of the other surface 490B connected thereto. The intervals between the respective claw portions 490 can be set at appropriate values. Further, a plurality of claw portions 490 are formed in the same way also on the surface (lower surface 43D shown in FIG. 4B) opposite to the surface (upper surface 43E) shown in FIG. 7 of the main body 43. At this time, in the end portion on the side opposite to the corner 43C of the upper surface 43E, claw portions 490A are formed in parallel to a line 470A perpendicular to a bisector of a vertical angle formed by a side surface 43A and the front surface 43F. As a result, the claw portions 490 and 490A formed on the upper surface 43E and the lower surface 43D are provided symmetrically with respect to a horizontal cut plane of the upper surface 43E and the lower surface 43D.

Since the claw portions 490 and 490A are formed at a predetermined slanting angle with respect to the side surfaces 43A and 43B of the intervertebral cage 41, the insertion direction of the intervertebral cage 41 is regulated. That is, the insertion direction is regulated in a direction B vertical to the cutting lines 470 and 470A (FIGS. 4A, 4B). Further, the intervertebral cage 41 can be inserted either in a left direction or in a right direction with respect to the vertebrae, depending on which surface of the upper and lower surfaces is faced upward.

Figure 8A:
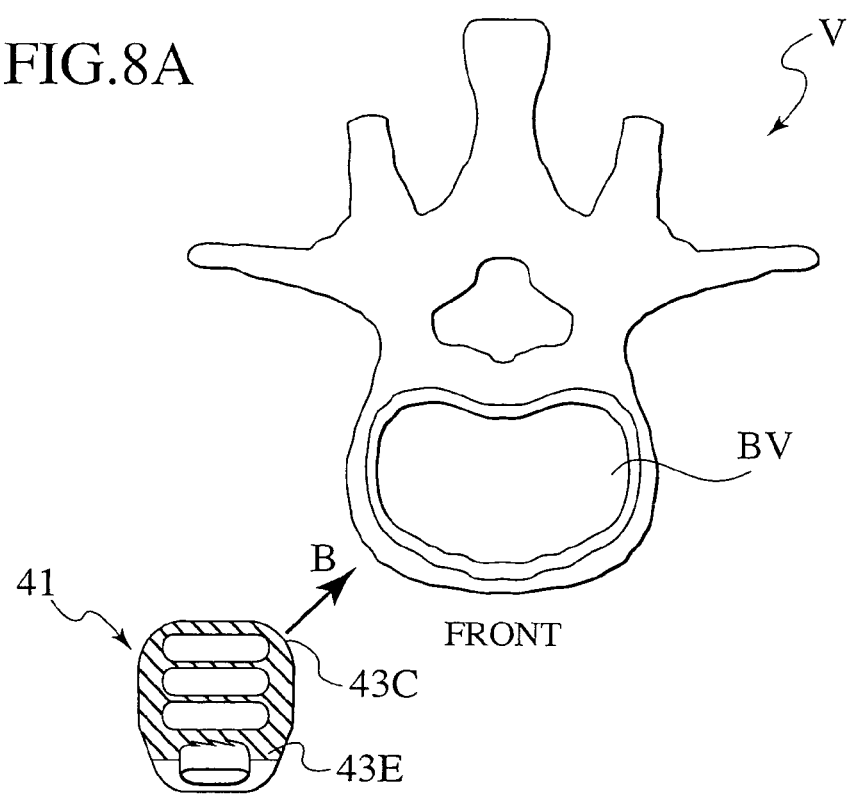
FIGS. 8A and 8B show an insertion direction of the intervertebral cage to vertebrae.
Figure 8B:
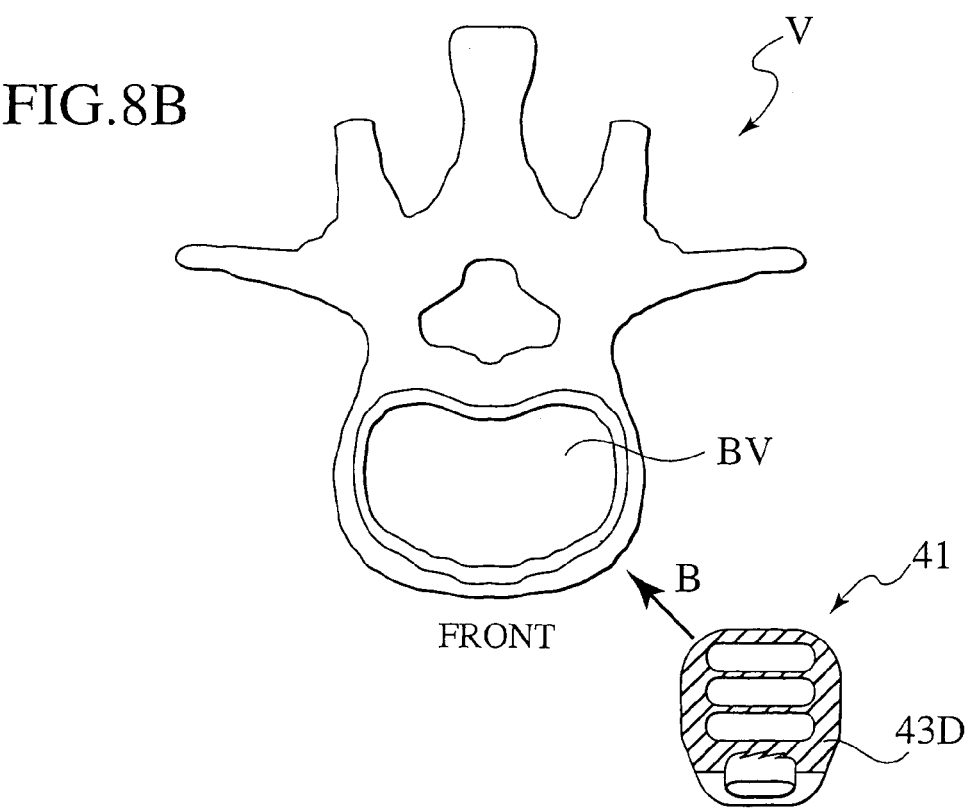

When the intervertebral cage 41 is inserted between the upper and lower vertebrae after the intervertebral disk is removed, the main body 43 is held by engaging a tool such as a pair of forceps with the transverse holes 45A, 47A and 49A and is inserted between the vertebrae BV from the left and front side of a spine V such that, as shown in FIG. 8A, the one corner 43C of the main body 43 goes ahead. By turning the intervertebral cage 41 upside down, as shown in FIG. 8B, the main body 43 can be inserted between the vertebrae BV from the right and front side.

Thus, even in a case where, for example, an organ is positioned in front of the spine, the main body 43 can be inserted between the vertebrae of the spine while avoiding the organ. At this time, in the main body 43, the rear end side is formed more thinly than the front end side, so that the main body 43 can be easily inserted between the vertebrae.

Further, after the main body 43 is inserted between the vertebrae, the cutting lines 470 and 470A of the plurality of claw portions 490 and 490A for preventing withdrawal, formed in the upper and lower surfaces 43D and 43E, bite into the end plates of the upper and lower vertebrae to thereby prevent the main body 43 from coming off between the vertebrae. Still further, by screwing implant screws S from the V-shaped groove 430 formed on the rear end surface of the main body 43 through the screw through holes 450U and 450L into the upper and lower vertebrae sandwiching the intervertebral cage 41, the main body 43 can be fixed between the upper and lower vertebrae with reliability. At this time, since the screw through holes 450U and 450L are elongated in lateral direction, the position into which the implant screws are screwed can be shifted in the longitudinal direction in response to the state of the vertebrae.

As described above, after the main body 43 is fixed between the upper and lower vertebrae, bone grows and gets into the front vertical hole 45, the center vertical hole 47 and the rear vertical hole 49, which are formed in the upper and lower surfaces of the main body 43 to thereby promote bone fusion. Then, it is possible to judge the bone fusion by passing X-rays through the transverse through holes 45A, 47A and 49A formed in correspondence to the respective vertical holes 45, 47 and 49 and taking an X-ray picture.

What is claimed is:

1. An intervertebral cage insertable between vertebrae of a spine comprising:
    a main body defined by a pair of upper and lower surfaces and a pair of side surfaces connected thereto; and
    a withdrawal prevention portion formed on the upper and/or the lower surfaces of the main body,
    wherein the withdrawal prevention portion regulates an insertion direction of the intervertebral cage,
    wherein the main body is formed in a hollow body and is made thicker on a rear side in the direction of insertion than on a front side,
    wherein the withdrawal prevention portion comprises a plurality of claw portions whose cutting lines are formed in a direction nearly perpendicular to a bisector line nearly bisecting an angle formed by a side surface and a front surface of the main body,
    and wherein a screw through hole is formed to pass through surfaces which form a V-shaped groove in a sectional side view in a rear end surface of the main body and are opposed to each other.

2. The intervertebral cage according to claim 1, wherein the screw through hole is an elongated hole made in a direction perpendicular to a longitudinal direction of the intervertebral cage.

3. The intervertebral cage according to claim 1, wherein the direction of insertion is regulated in a direction perpendicular to the cutting lines.

4. The intervertebral cage according to claim 1, wherein the main body has a vertical through hole passing through the upper and lower surfaces, a transverse through hole passing through the side surfaces from one side to the other side, and a hole formed from a front end surface in a direction of insertion of the main body to a rear end surface opposite to the front end surface.

* * * * *